United States Patent
Hansis et al.

(10) Patent No.: US 10,552,958 B2
(45) Date of Patent: Feb. 4, 2020

(54) FRACTIONAL FLOW RESERVE DETERMINATION

(71) Applicant: KONINKLIJKE PHILIPS N.V., Eindhoven (NL)

(72) Inventors: Eberhard Sebastian Hansis, Hamburg (DE); Holger Schmitt, Hamburg (DE); Michael Grass, Buchholz in der Nordheide (DE); Dirk Schaefer, Hamburg (DE); Hanno Heyke Homann, Hannover (DE); Tobias Klinder, Uelzen (DE); Christian Haase, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 177 days.

(21) Appl. No.: 15/570,620

(22) PCT Filed: Apr. 26, 2016

(86) PCT No.: PCT/EP2016/059248
§ 371 (c)(1),
(2) Date: Oct. 30, 2017

(87) PCT Pub. No.: WO2016/174010
PCT Pub. Date: Nov. 3, 2016

(65) Prior Publication Data
US 2018/0286045 A1 Oct. 4, 2018

(30) Foreign Application Priority Data
Apr. 30, 2015 (EP) .................................... 15165960

(51) Int. Cl.
*G06K 9/00* (2006.01)
*G06T 7/00* (2017.01)
(Continued)

(52) U.S. Cl.
CPC ............ *G06T 7/0016* (2013.01); *A61B 5/026* (2013.01); *A61B 5/02158* (2013.01);
(Continued)

(58) Field of Classification Search
None
See application file for complete search history.

(56) References Cited

U.S. PATENT DOCUMENTS

| 2013/0246034 A1* | 9/2013 | Sharma | A61B 5/02007 |
| | | | 703/11 |
| 2014/0114185 A1 | 4/2014 | Tolkowsky | |

(Continued)

OTHER PUBLICATIONS

Tar, B. et al. "The effect of the sensor position of the pressure wire distal to a coronary stenosis on the calculated fractional flow reserve" Computing in Cardiology 2013; pp. 1099-1102 N/A, (Sep. 22, 2013).

(Continued)

*Primary Examiner* — Shervin K Nakhjavan (57) ABSTRACT

The present invention relates to a device (1) for fractional flow reserve determination, the device (1) comprising: a model source (10) configured to provide a first three-dimensional model (3DM1) of a portion of an imaged vascular vessel tree (VVT) surrounding a stenosed vessel segment (SVS) and configured to provide a second three-dimensional model (3DM2) of a pressure wire insertable into the vascular vessel tree (VVT); and a processor (20) configured to calculate a first blood flow (Q1) through the stenosed vessel segment (SVS) with the pressure wire (PW) inserted into the vascular vessel tree (VVT) based on the first and the second three-dimensional model and to calculate a second blood flow (Q2) through the stenosed vessel segment (SVS) without the pressure wire (PW) inserted into the vascular vessel tree (VVT) based on the first three-dimensional model (3DM1) and to determine a first fractional flow reserve value (FFR1) to be measured with the pressure wire (PW) inserted into the vascular vessel tree (VVT) based on the first blood flow (Q1) and to determine a second fractional flow reserve value (FFR2) to be measured without the (Continued)

pressure wire (PW) inserted into the vascular vessel tree (VVT) based on the second blood flow (Q1).

15 Claims, 8 Drawing Sheets

(51) Int. Cl.
    *G06T 17/20*     (2006.01)
    *A61B 5/0215*     (2006.01)
    *A61B 5/026*     (2006.01)
    *A61B 5/00*     (2006.01)
    *A61B 6/03*     (2006.01)
    *A61B 6/00*     (2006.01)
    *G06T 7/60*     (2017.01)

(52) U.S. Cl.
    CPC ............ *A61B 5/6851* (2013.01); *A61B 6/032* (2013.01); *A61B 6/466* (2013.01); *A61B 6/504* (2013.01); *G06T 7/60* (2013.01); *G06T 17/20* (2013.01); *G06T 2207/10081* (2013.01); *G06T 2207/30104* (2013.01)

(56) References Cited

U.S. PATENT DOCUMENTS

| | | | |
|---|---|---|---|
| 2014/0121513 A1 | 5/2014 | Tolkowsky | |
| 2014/0228684 A1 | 8/2014 | Kassab | |
| 2014/0236011 A1* | 8/2014 | Fan | A61B 5/6876 600/440 |
| 2014/0249784 A1 | 9/2014 | Sankaran et al. | |
| 2014/0276137 A1* | 9/2014 | Burnett | A61B 5/0215 600/486 |
| 2015/0257655 A1* | 9/2015 | Ishii | A61B 5/02007 600/508 |
| 2015/0265222 A1* | 9/2015 | Sakaguchi | A61B 6/032 600/407 |
| 2015/0324962 A1* | 11/2015 | Itu | G06T 7/00 382/130 |
| 2015/0348260 A1* | 12/2015 | Sharma | G06T 7/0012 600/480 |
| 2016/0070877 A1* | 3/2016 | Taylor | A61B 5/7275 703/9 |
| 2019/0110776 A1* | 4/2019 | Yu | A61B 8/5246 |

OTHER PUBLICATIONS

Roy, et al. "Delineating the guide-wire flow obstruction effect in assessment of fractional flow reserve and coronary flow reserve measurements" Am. J. Physiol. Heart Circ/ Physiol 289: H392-H397, (Feb. 25, 2005).

Tu, et al. "Fractional Flow Reserve Calculation from 3 Dimensional Quantitative Coronary Angiography and TIMI Frame Count" JACC: Cardiovascular Interventions vol. 7. No. 7, pp. 768-777 (Jul. 2014).

* cited by examiner

FRACTIONAL FLOW RESERVE DETERMINATION

FIELD OF THE INVENTION

The present invention relates to the field of coronary angiography. In particular, the present invention relates to a device and a method for fractional flow reserve determination.

BACKGROUND OF THE INVENTION

Coronary angiography allows for excellent visualization of coronary arteries. However, assessment of functional stenosis severity is limited. Fractional flow reserve, FFR, is a reliable measure for grading stenosis. Based on the aortic pressure $P_a$ and the pressure $P_d$ distal to the stenosis, FFR is defined as: $FFR=P_d/P_a$.

FFR is a widely used index to assess the functional impact of a stenosis in the coronary arteries. Typically, FFR is measured in an invasive fashion, by advancing a pressure wire past the stenosis and measuring the pressure drop across the stenosis. In recent years, non-invasive determination of FFR has been pursued, using fluid-dynamics simulations of blood flow based on CT angiography images.

SUMMARY OF THE INVENTION

There may be a need to improve devices and methods for fractional flow reserve determination.

This is met by the subject-matter of the independent claims. Further exemplary embodiments are evident from the dependent claims and the following description.

The present invention relates to a device for fractional flow reserve determination, the device comprising: a model source configured to provide a first three-dimensional model of a portion of an imaged vascular vessel tree surrounding a stenosed vessel segment and configured to provide a second three-dimensional model of a pressure wire insertable into the vascular vessel tree; a processor configured to calculate a first blood flow through the stenosed vessel segment with the pressure wire inserted into the vascular vessel tree based on the first and the second three-dimensional model and to calculate a second blood flow through the stenosed vessel segment without the pressure wire inserted into the vascular vessel tree based on the first three-dimensional model and to determine a first fractional flow reserve value to be measured with the pressure wire inserted into the vascular vessel tree based on the first blood flow and to determine a second fractional flow reserve value to be measured without the pressure wire inserted into the vascular vessel tree based on the second blood flow. The imaged vascular vessel tree may be modeled by creating a three-dimensional model representing at least a portion of the vascular vessel tree of a patient.

According to the invention, a three-dimensional model of the pressure wire, which is present in a stenosed vessel during pressure measurements in conventional FFR, may be introduced into a simulation of the fractional flow reserve.

The present invention advantageously provides that the pressure wire is taken into account in the image-based FFR simulations for an improved accuracy of the simulation and for an improved determination of the impact of the pressure wire.

The present invention advantageously provides a model of the pressure wire that is included in fluid dynamics FFR simulations. Using the model, the changes in FFR resulting from the introduced wire are estimated. The simulated FFR values with and without wire are presented to the user together with supporting data. These serve to enable accurate comparison to invasively measured FFR values and assess the impact of the pressure wire on the invasively measured FFR value.

The present invention advantageously provides an approach to FFR, which allows improving the reliability of catheterized FFR measurements. The present invention advantageously provides to introduce virtual FFR into existing systems and enhance the acceptability of virtual FFR.

According to a further, second aspect of the present invention, a medical imaging system is provided comprising a display device and a device according to the first aspect of the present invention or according to any implementation form of the first aspect of the present invention. The display device is configured to display the first fractional flow reserve value and/or the second fractional flow reserve value.

According to a further, third aspect of the present invention, a method for fractional flow reserve determination is provided, the method comprising the steps of:

a) providing a first three-dimensional model of a portion of an imaged vascular vessel tree surrounding a stenosed vessel segment and providing a second three-dimensional model of a pressure wire insertable into the vascular vessel tree by a model simulator;

b) calculating a first blood flow through the stenosed vessel segment with the pressure wire inserted into the vascular vessel tree based on the first and the second three-dimensional model and calculating a second blood flow through the stenosed vessel segment without the pressure wire inserted into the vascular vessel tree based on the first three-dimensional model by a processor; and c) determining a first fractional flow reserve value to be measured with the pressure wire inserted into the vascular vessel tree based on the first blood flow and determining a second fractional flow reserve value to be measured without the pressure wire inserted into the vascular vessel tree based on the second blood flow by the processor.

According to an exemplary embodiment of the present invention, the model source is configured to receive the first three-dimensional model and the second three-dimensional model from a database coupled to the device. This advantageously provides an implementation of externally calculated three-dimensional models.

According to an exemplary embodiment of the present invention, the model source is configured to generate the first three-dimensional model and the second three-dimensional model. This advantageously provides an autonomously processing by using internally calculated three-dimensional models.

According to an exemplary embodiment of the present invention, the processor is configured calculate the first blood flow and to calculate the second blood flow using a finite element modeling. This advantageously provides an improved fluid dynamics simulation based on three-dimensional volumetric mesh.

The term "finite element modelling" or "finite element method" as used by the present invention may refer to a numerical calculation and determination for finding approximate solutions to boundary value problems for partial differential equations, as for instance to be solved in the field of fluid dynamics FFR. The numerical technique may use a subdivision of a whole problem domain into simpler parts, called finite elements, and variational methods from the calculus of variations to solve the problem by minimizing an associated error function.

According to an exemplary embodiment of the present invention, the processor is configured calculate the first blood flow and to calculate the second blood flow using a lumped element modelling.

This advantageously provides a reliable and normalized fractional-flow-reserve determination.

The term "lumped element modelling" as used by the present invention may refer to a parameter model or a lumped component model that models a response of a spatially distributed system of elements into a topology comprising functional entities that approximate the function of the modeled elements. In other words, the lumped element modeling may be used to calculate fluid dynamics based on a volumetric three-dimensional model.

According to an exemplary embodiment of the present invention, the model source is configured to provide the first three-dimensional model and/or the second three-dimensional model using a volumetric mesh. This advantageously improves the accuracy of the blood flow detection, simulation, and measurement.

The term "volumetric meshes" as used by the present invention may refer to a polygonal representation of the interior volume of an object. Volumetric meshes may also discretize the interior structure of the object. In an example, volumetric meshes may be represented by finite element methods or by finite element analysis, which may use regular or irregular volumetric meshes to compute internal stresses and forces in an object throughout the entire volume of the object.

According to an exemplary embodiment of the present invention, the model source is configured to provide the first three-dimensional model and/or the second three-dimensional model using a pre-computed building block. This advantageously also improves the accuracy of the blood flow detection, simulation, and measurement.

According to an exemplary embodiment of the present invention, the processor is configured to calculate the first blood flow through the stenosed vessel segment with the pressure wire inserted into the vascular vessel tree using in addition to the geometric model:

(i) a geometric dimension of the pressure wire; or
(ii) an elastomechanical property of the pressure wire; or
(iii) a surface roughness property of the pressure wire; or
(iv) a material property of the pressure wire. This advantageously also improves the accuracy of the blood flow detection and measurement. The term "geometric model" as used by the present invention may refer to the first and/or the second three-dimensional model or any further calculated geometric model of a vessel or a catheter or a device configured to be inserted into a blood vessel.

According to an exemplary embodiment of the present invention, the model source is configured to provide the first three-dimensional model of a portion of the imaged vascular vessel tree surrounding a stenosed vessel segment based on image data of X-ray angiography or on three-dimensional volume data of computed tomography. Advantageously, this improves the accuracy of the blood flow detection, simulation and measurement, too.

According to an exemplary embodiment of the present invention the model source is configured to provide the second three-dimensional model of the pressure wire based on image data of X-ray angiography or based on data about geometrical dimensions of the pressure wire. Improving the accuracy of the blood flow detection, simulation and measurement is advantageously also achieved.

The foregoing has outlined rather broadly the features and technical advantages of the present invention in order that the detailed description of the embodiments that follow may be better understood. Additional features and advantages of the embodiments will be described hereinafter which form the subject of the claims of the present invention.

It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the scope of the invention as set forth in the appended claims.

These and other aspects of the present invention will become apparent from and be elucidated with reference to the embodiments described hereinafter.

BRIEF DESCRIPTION OF THE DRAWINGS

A more complete appreciation of the present invention and the attendant advantages thereof will be more clearly understood with reference to the following schematic drawings, which are not to scale, wherein.

DETAILED DESCRIPTION OF EMBODIMENTS

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

The model of the pressure wire represents the geometric dimensions of a typical pressure wire. The wire location can be predicted using elasto-mechanic models of the wire and the vessel and this way can be included in the FFR simulation.

The FFR simulation can be carried out by full finite-element modeling, FEM, or with non-specific methods like lumped models combining flow properties of shortened "building blocks" of vessel sections. The wire can be incorporated in both type of modeling methods, by including it in the volumetric mesh of the FEM or by incorporating it in the pre-computed building blocks of the lumped model. One possible approach would be to consider the wire as a reduction of the vessel's cross-sectional area.

The improved FFR estimate with the wire present in the simulation may be presented to the user using a display, alongside the simulated value without wire present. The impact of the pressure wire on the FFR can be displayed to the user by the two values.

By combining an invasive FFR measurement with the proposed image-derived FFR, wherein image-derived FFR corresponds to the situation without an inserted pressure wire, the impact of the inserted pressure wire on the invasively measured FFR value. This impact corresponds to the difference of the FFR value between with and without the pressure wire, in other words, allows the precise determination of the physiologically correct FFR without a pressure wire present, based on simulations with and without pressure wire. This allows indicating to an user if an invasively measured FFR value might be unreliable or not representative of the physiologic flow reserve without the wire due to the introduction of the pressure wire.

Figure 1:
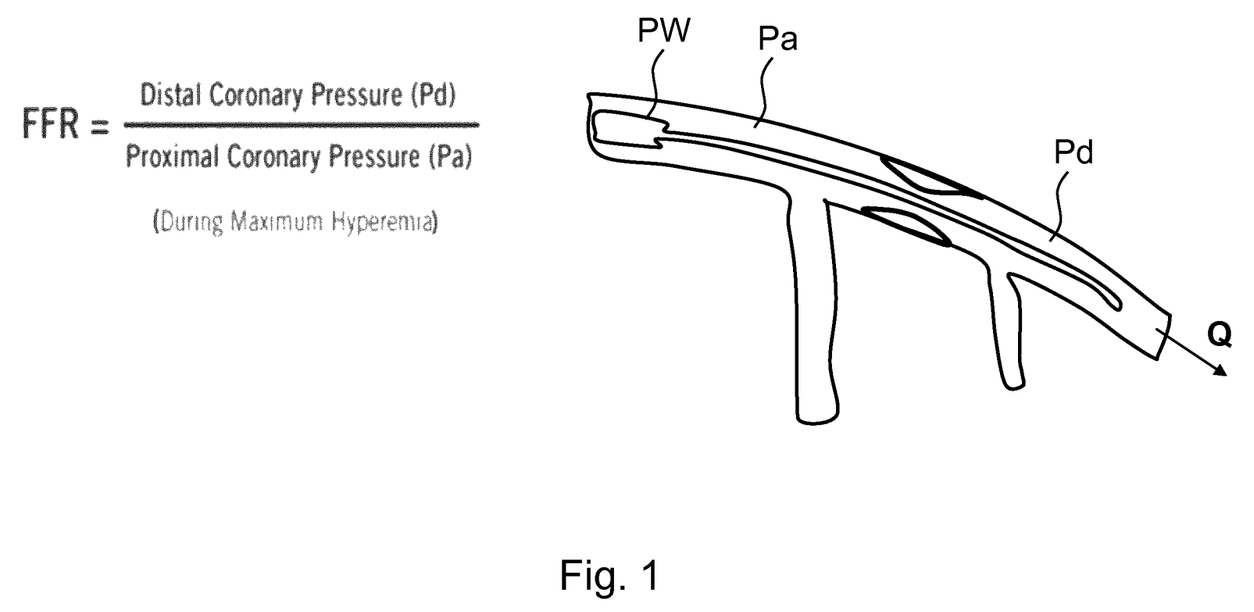
FIG. 1 shows a schematic diagram of region of a vascular vessel tree for explaining the present invention.

FIG. 1 shows a schematic diagram of region of a vascular vessel tree for explaining the present invention.

On the left side of FIG. 1, the formula of the fractional flow reserve FFR is shown. The blood flow Q through the stenosis and the aortic pressure $p_a$ may be known, a model of the stenosed vessel segment alone can be used to calculate the distal pressure $p_d$. This can be achieved via a full three-dimensional computational fluid dynamics simulation or by a lumped components approach where the segment's resistance is approximated from its cross-sectional areas, considering the Poiseuille effect (or Poiseuille's Law), the Bernoulli principle and others. Then, the fractional flow reserve FFR can be calculated as in the following equation as illustrated in FIG. 1:

$$FFR=P_d/P_a.$$

In FIG. 1, on the right side, an invasive measurement of FFR is shown, a pressure wire PW is advanced through the stenosis to measure the blood pressure on both sides of the stenosis. The presence of the pressure wire PW within the vessel lumen modifies the blood flow, thereby influencing the FFR measurement. The pressure wire PW may be a tubular device or an in a blood vessel insertable device configured to measure pressure, e.g. intravascular pressure, temperature and thermodilution flow.

According to an exemplary embodiment of the present invention, the pressure wire PW may be in form of a catheter and may be configured to measure the pressure difference across a stenosis to determine, for instance, if it reduces blood flow to the heart muscle. For this purpose, the pressure wire PW may comprise multiple pressure or temperature sensors along its longitudinal extension or the pressure wire PW may be moved and record subsequently measurements of the pressure or the temperature with a single sensor, for instance, located at the tip.

According to an exemplary embodiment of the present invention, the pressure wire PW may be configured to provide a pressure field, e.g. a spatially resolved pressure distribution inside the blood vessel. Based on the recorded measurements, the physiologically relevant FFR value without the pressure wire PW present can be estimated with the present method.

According to an exemplary embodiment of the present invention, the pressure wire PW may be advanced distally to the stenosis. Then, the proximal coronary pressure may be recorded by the guiding catheter in form of the pressure wire PW. For instance, both distal and proximal pressures may be measured by the pressure wire PW during hyperemia.

According to an exemplary embodiment of the present invention, during the invasive measurement the pressure wire is present in the vessel, which reduces the effective vessel lumen. This is particularly relevant for a highly stenotic region, where even the introduction of the thin (sub-mm diameter) pressure wire may result in a substantial relative change of lumen cross-section.

According to an exemplary embodiment of the present invention, a typical FFR or pressure wire PW of 0.36 mm diameter corresponds to 30% of the diameter and 9% of the lumen cross-sectional area in a 60% stenosis of a 3 mm diameter vessel. Its fluid-dynamic impact may be disproportionally higher, owing to the localized nature of the introduced obstacle. The present invention enables the computation of FFR values with and without a pressure wire, and hence estimating its impact on FFR.

Figure 2:
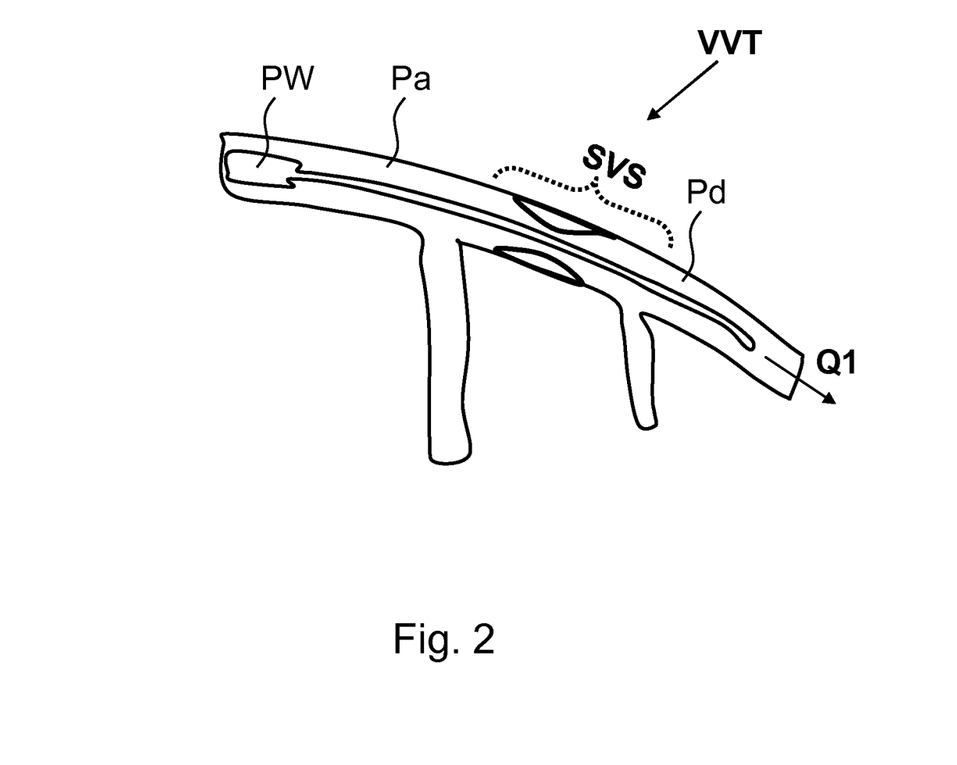
FIG. 2 shows a schematic diagram of region of a vascular vessel tree for explaining the present invention.

In non-invasive, image-based methods, on the contrary, no wire is present (FIG. 2). It is desired to produce comparable FFR measurements with both invasive and non-invasive methods, in order to be able to use established standards of care for invasive measurements also for image-based measurements. Therefore, it is proposed that the pressure wire is taken into account in the image-based FFR simulations for better comparability of the two methods.

Although guide wires can be used, in principle, to measure velocity, flow and FFR, absolute measurements of flow are more difficult because of uncertainties in velocity, transducer positioning and sample volume, determination of accurate luminal area, and in vivo calibration. Therefore, measuring of the pressure provides an improve accuracy and the blood flow and the FFR is calculated using the determined pressure values as input.

According to an exemplary embodiment of the present invention, a model of the pressure wire PW is included in fluid dynamics FFR simulations using finite element methods or finite element modelling. Using the model, the changes in FFR resulting from the introduced wire are estimated. The simulated FFR values with and without wire are presented to the user together with supporting data. These serve to enable accurate comparison to invasively measured FFR values and assess the impact of the pressure wire on the invasively measured FFR value. Different embodiments of the invention are envisioned:

The model of the pressure wire represents the geometric dimensions of a typical pressure wire. It may contain information about the wire's elasto-mechanical properties, surface roughness, or other material properties. The effect of the pressure wire PW on blood flow may depend on the wire's location in each section of the vessel—whether the wire is located near the center of the lumen, running along its wall, or being pressed into the wall.

The wire location can be predicted using elasto-mechanic models of the wire and the vessel and this way can be included in the FFR simulation using finite element methods or finite element modelling. Alternatively, a range of values for the simulated FFR can be computed, representing different location configurations of the wire or of other variable wire properties. Alternatively the wire location can be determined from angiography images.

FIG. 2 shows a schematic diagram of region of a vascular vessel tree for explaining the present invention. FIG. 2 shows a corresponding situation as shown in FIG. 1 with the pressure wire PW being inserted into the stenosed vessel segment SVS of the vascular vessel tree VVT. In FIG. 2, a first blood flow Q1 passes through the stenosed vessel segment SVS with the pressure wire PW being inserted into the vascular vessel tree VVT.

Figure 3:
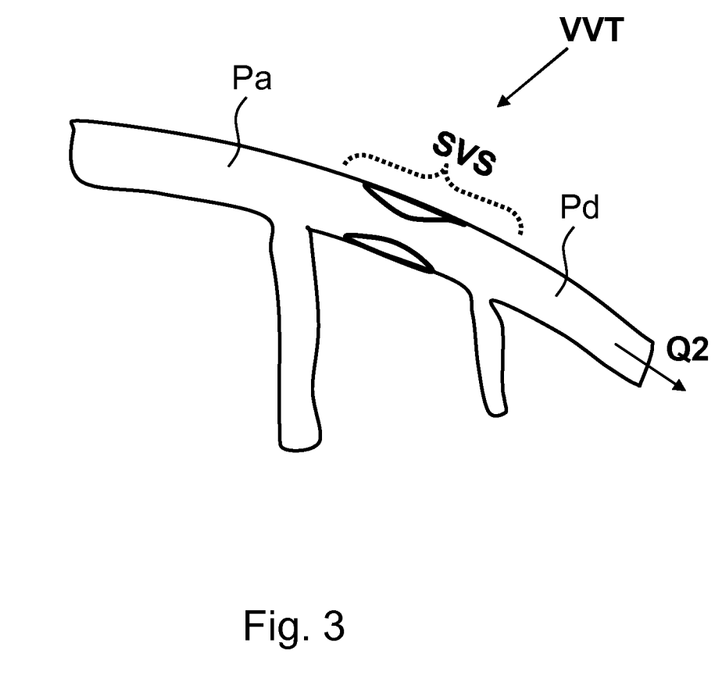
FIG. 3 shows a schematic diagram of region of a vascular vessel tree for explaining the present invention.

FIG. 3 shows a schematic diagram of region of a vascular vessel tree for explaining the present invention. FIG. 3 shows a non-equivalent situation as shown in FIG. 1 or 2 with the pressure wire PW being not inserted into the stenosed vessel segment SVS of the vascular vessel tree VVT, e.g. an empty stenosed vessel segment. In FIG. 3, a second blood flow Q2 passes through the stenosed vessel segment SVS without the pressure wire PW being inserted into the vascular vessel tree VVT.

Figure 4:
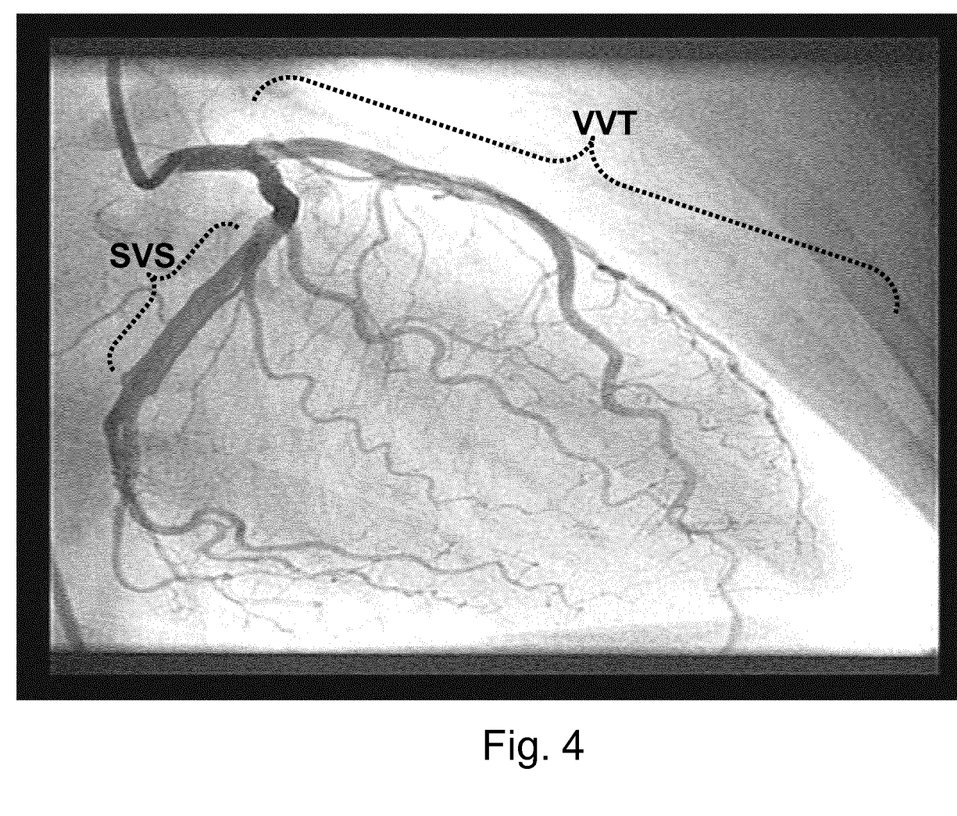
FIG. 4 shows a schematic diagram of an image of a coronary vessel tree for explaining the present invention.

FIG. 4 shows a schematic diagram of an image of a coronary vessel tree for explaining the present invention. FIG. 4 shows an imaged stenosed vessel segment SVS of the vascular vessel tree VVT.

Figure 5:
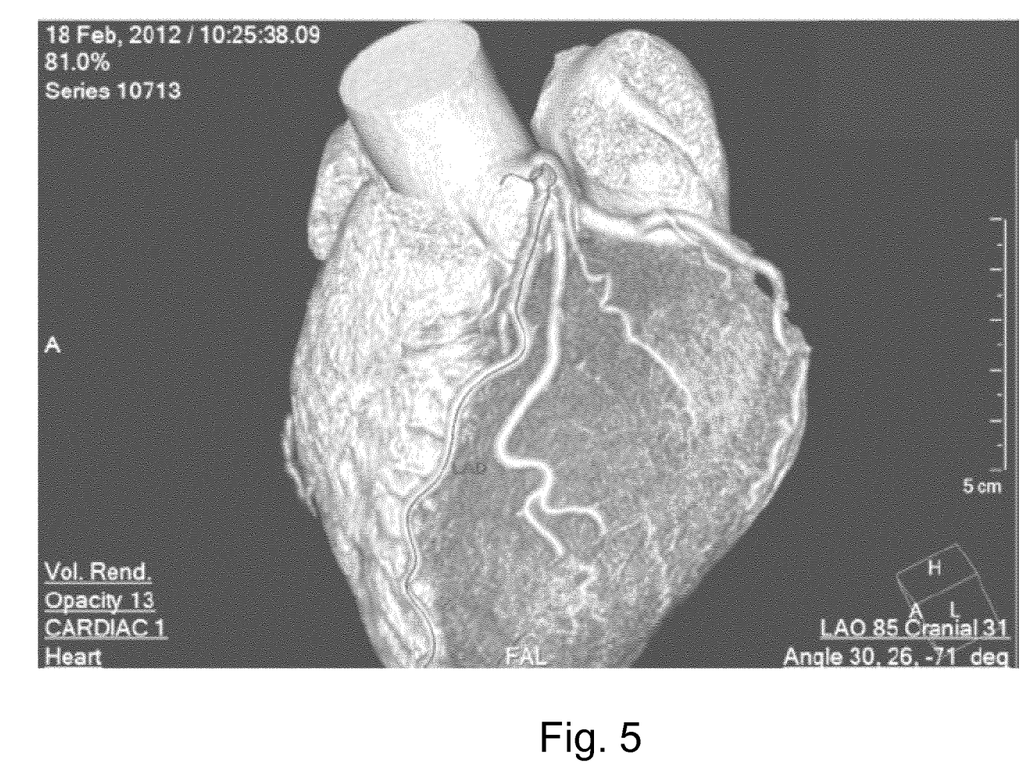
FIG. 5 shows a schematic diagram of an image of a coronary vessel tree for explaining the present invention.

FIG. 5 shows a schematic diagram of an image of a coronary vessel tree for explaining the present invention. The image as shown in FIG. 5 may be based, for instance, on image data as acquired by an X-ray guided cardiac medical intervention device, by a CT-imaging system or by a magnetic resonance (MR) angiography imaging system or by an intravascular ultra sound system.

Figure 6:
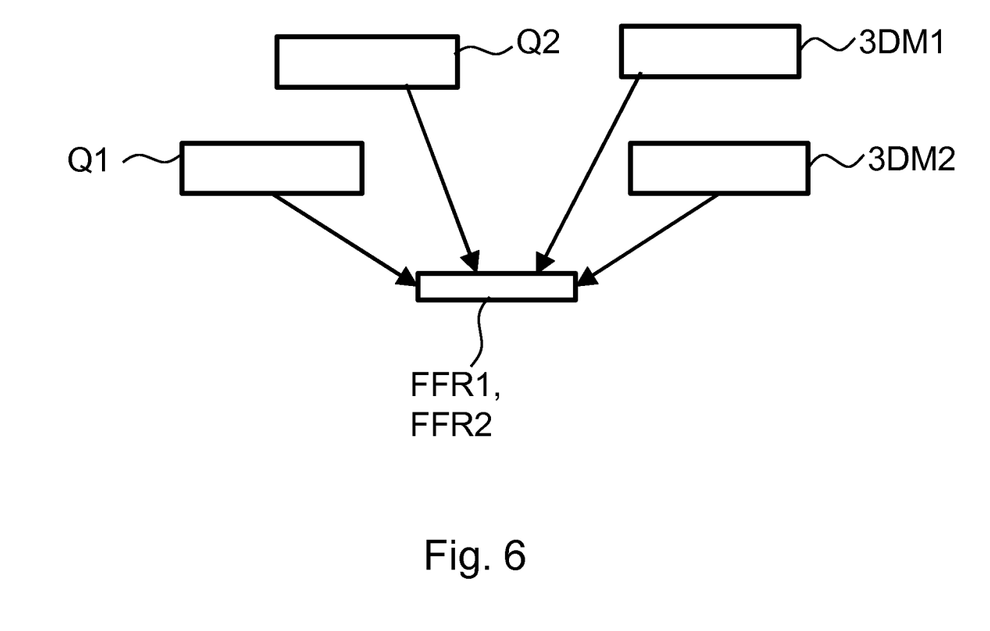
FIG. 6 shows a schematic diagram of a flowchart diagram according to an exemplary embodiment of the present invention.

FIG. 6 shows a schematic diagram of a flowchart diagram for explaining the present invention.

Initially, a first three-dimensional model 3DM1 of a portion of an imaged vascular vessel tree VVT surrounding a stenosed vessel segment SVS and a second three-dimensional model 3DM2 of a pressure wire PW insertable into the vascular vessel tree VVT may be calculated.

Then, a first blood flow Q1 through the stenosed vessel segment SVS with the pressure wire PW inserted into the vascular vessel tree VVT and a second blood flow Q2 through the stenosed vessel segment SVS without the pressure wire PW may be calculated. The calculation may be performed by three-dimensional modeling using finite element methods or finite element modeling.

Subsequently, a first fractional flow reserve value FFR1 to be measured with the pressure wire PW inserted into the vascular vessel tree VVT based on the first blood flow Q1 and a second fractional flow reserve value FFR2 to be measured without the pressure wire PW inserted into the vascular vessel tree VVT based on the second blood flow Q2 may be determined.

Figure 7:
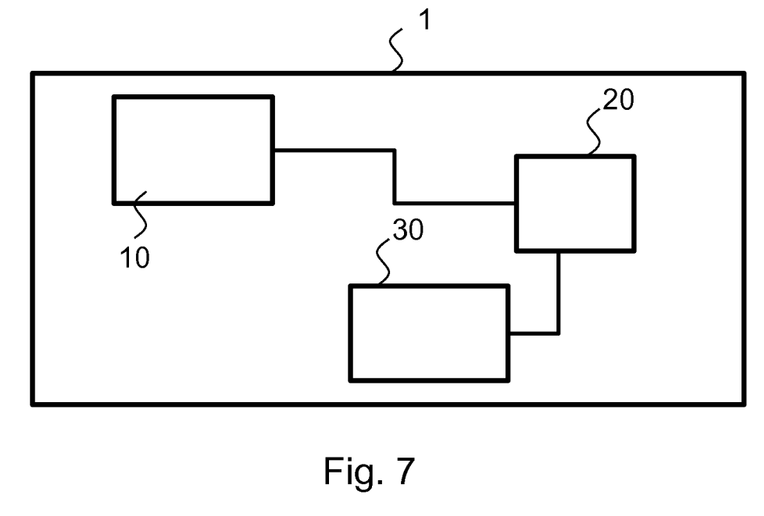
FIG. 7 shows a schematic diagram of a device for fractional flow reserve determination according to an exemplary embodiment of the present invention.

FIG. 7 shows a schematic diagram of a device 1 for fractional flow reserve determination according to an exemplary embodiment of the present invention.

The device 1 for fractional flow reserve determination may comprise a model simulator 10, a processor 20.

The model source 10 may be configured to provide a first three-dimensional model 3DM1 of a portion of an imaged vascular vessel tree VVT surrounding a stenosed vessel segment SVS and configured to provide a second three-dimensional model 3DM2 of a pressure wire insertable into the vascular vessel tree VVT.

According to an exemplary embodiment of the present invention, the model source 10 may be configured to receive predefined models, e.g. a predefined first three-dimensional model 3DM1 and a predefined second three-dimensional model 3DM2 both of which may be for instance pre-programmed in the workstation and retrieved as necessary. In other words, the module source 10 can be coupled to a database comprising a plurality of three-dimensional models 3DM1, 3DM2. The database may provide pre-calculated three-dimensional models of various pressure wires PW as available for interventional procedures or a plurality of pre-calculated three-dimensional models of vessel structures of a patient based on previously recorded imaging data for a specific patient.

According to an exemplary embodiment of the present invention, the model source 10 may be configured to generate the three-dimensional models 3DM1, 3DM2, e.g. generating the first three-dimensional model 3DM1 and generating the second three-dimensional model 3DM2.

The processor 20 may be configured to calculate a first blood flow Q1 through the stenosed vessel segment SVS with the pressure wire PW inserted into the vascular vessel tree VVT based on the first and the second three-dimensional model and to calculate a second blood flow Q2 through the stenosed vessel segment SVS without the pressure wire PW inserted into the vascular vessel tree VVT based on the first three-dimensional model.

The processor 20 may be configured to determine a first fractional flow reserve value FFR1 representing a value to be measured with the pressure wire PW inserted into the vascular vessel tree VVT based on the first blood flow Q1 and to determine a second fractional flow reserve value FFR2 representing a value to be measured without the pressure wire PW inserted into the vascular vessel tree VVT based on the second blood flow Q2.

Figure 8:
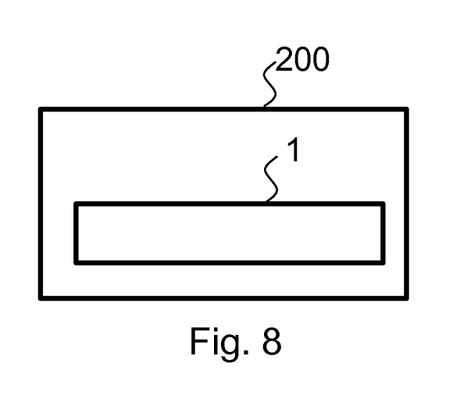
FIG. 8 shows a schematic diagram of a medical imaging system according to an exemplary embodiment of the present invention.

FIG. 8 shows a schematic diagram of a medical imaging system 200 according to an exemplary embodiment of the present invention.

The medical imaging system 200 may comprise an example of the device 1 for fractional flow reserve determination. The medical imaging system 200 may be an X-ray guided cardiac medical intervention device, a CT-imaging system or a magnetic resonance (MR) angiography imaging system or an intravascular ultra sound system.

Further, the medical imaging system 200 may be used for coronary flow reserve determination.

Figure 9:
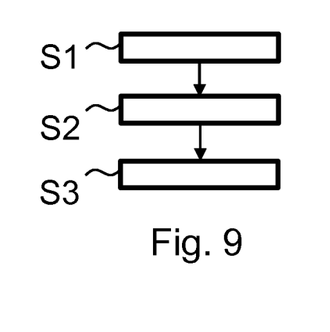
FIG. 9 shows a schematic diagram of a flowchart diagram of a method for fractional flow reserve determination according to an exemplary embodiment of the present invention.

FIG. 9 shows a schematic diagram of a flowchart of a method for fractional flow reserve determination. The method for fractional flow reserve determination may comprise the following steps:

As a first step a) of the method, providing S1 a first three-dimensional model 3DM1 of a portion of an imaged vascular vessel tree VVT surrounding a stenosed vessel segment SVS and providing a second three-dimensional model 3DM2 of a pressure wire insertable into the vascular vessel tree VVT by a model source 10 may be conducted.

As a second step b) of the method, calculating S2 a first blood flow Q1 through the stenosed vessel segment SVS with the pressure wire PW inserted into the vascular vessel tree VVT based on the first three-dimensional model 3DM1 and the second three-dimensional model 3DM2 and calculating a second blood flow Q2 through the stenosed vessel segment SVS without the pressure wire PW inserted into the vascular vessel tree VVT by a processor 20 based on the first three-dimensional model 3DM1 may be conducted.

As a third step c) of the method, determining S3 a first fractional flow reserve value FFR1 to be measured with the pressure wire PW inserted into the vascular vessel tree VVT based on the first blood flow Q1 and determining a second fractional flow reserve value FFR2 to be measured without the pressure wire PW inserted into the vascular vessel tree VVT based on the second blood flow Q2 by the processor 20 may be conducted.

It has to be noted that embodiments of the present invention are described with reference to different subject-matters. In particular, some embodiments are described with reference to method type claims whereas other embodiments are described with reference to device type claims.

However, a person skilled in the art will gather from the above and the foregoing description that, unless otherwise notified, in addition to any combination of features belonging to one type of the subject-matter also any combination between features relating to different subject-matters is considered to be disclosed with this application.

However, all features can be combined providing synergetic effects that are more than the simple summation of these features.

While the present invention has been illustrated and described in detail in the drawings and the foregoing description, such illustration and description are to be considered illustrative or exemplary and not restrictive; the present invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for fractional flow reserve determination, the device comprising:
    a processor configured to:
        provide a first three-dimensional model of a portion of an imaged vascular vessel tree surrounding a stenosed vessel segment;
        provide a second three-dimensional model of a pressure wire insertable into the vascular vessel tree
        calculate a first blood flow through the stenosed vessel segment with the pressure wire present in the vascular vessel tree based on the first three-dimensional model and second three-dimensional model;
        calculate a second blood flow through the stenosed vessel segment without the pressure wire present in the vascular vessel tree based on the first three-dimensional model only; and
        determine a first fractional flow reserve value based on the first blood flow and a second fractional flow reserve value based on the second blood flow.

2. Device according to claim 1,
    wherein the processor is configured to receive the first three-dimensional model and the second three-dimensional model from a database coupled to the device.

3. Device according to claim 1,
    wherein the processor is configured to generate the first three-dimensional model and the second three-dimensional model.

4. Device according to claim 3,
    wherein the first three-dimensional model and/or the second three-dimensional model is generated using a volumetric mesh.

5. Device according to claim 3,
    wherein the first three-dimensional model and/or the second three-dimensional model is generated using a pre-computed building block.

6. Device according to claim 3,
    wherein the processor is configured to generate the first three-dimensional model of the portion of the imaged vascular vessel tree surrounding the stenosed vessel segment based on image data of X-ray angiography or on three-dimensional volume data of computed tomography.

7. Device according to claim 3,
    wherein the processor is configured to generate the second three-dimensional model of the pressure wire based on image data of X-ray angiography or based on data about geometrical dimensions of the pressure wire.

8. Device according to claim 1,
    wherein the processor is configured to calculate the first blood flow and to calculate the second blood flow using a finite element modelling.

9. Device according to claim 1,
    wherein the processor is configured to calculate the first blood flow and to calculate the second blood flow using a lumped element modelling.

10. Device according to claim 1,
    wherein the processor is configured to calculate the first blood flow through the stenosed vessel segment with the pressure wire inserted into the vascular vessel tree using, in addition to the first three-dimensional model and the second three-dimensional model:
        a geometric dimension of the pressure wire; or
        an elastomechanical property of the pressure wire; or
        a surface roughness property of the pressure wire; or
        a material property of the pressure wire.

11. A medical imaging system comprising:
    a display device; and
    the device according to claim 1,
    wherein the display device is configured to display the first fractional flow reserve value and/or the second fractional flow reserve value.

12. A method for fractional flow reserve determination, the method comprising the steps of:
    providing, by a processor, a first three-dimensional model of a portion of an imaged vascular vessel tree surrounding a stenosed vessel segment;
    providing, by the processor, a second three-dimensional model of a pressure wire insertable into the vascular vessel tree;
    calculating, by the processor, a first blood flow through the stenosed vessel segment with the pressure wire present in the vascular vessel tree based on the first and the second three-dimensional model;
    calculating, by the processor, a second blood flow through the stenosed vessel segment without the pressure wire present in the vascular vessel tree based on the first three-dimensional model only; and
    determining, by the processor, a first fractional flow reserve value based on the first blood flow and determining a second fractional flow reserve value based on the second blood flow.

13. Method according to claim 12,
    wherein the steps of calculating the first blood flow and calculating the second blood flow comprise using a finite element modelling; and/or
    wherein the steps of calculating the first blood flow and calculating the second blood flow comprises using a lumped element modelling.

14. Method according to claim 12,
    wherein the steps of providing the first three-dimensional model and providing the second three-dimensional model comprise using a volumetric mesh; and/or
    wherein the steps of providing the first three-dimensional model and providing the second three-dimensional model comprises using a pre-computed building block.

15. Method according to claim 12,
wherein the step of calculating the first blood flow through the stenosed vessel segment with the pressure wire inserted into the vascular vessel tree comprises using in addition to the first three-dimensional model and the second three-dimensional model:
a geometric dimension of the pressure wire; or
an elastomechanical property of the pressure wire; or
a surface roughness property of the pressure wire; or
a material property of the pressure wire.

* * * * *